United States Patent [19]
Kawai et al.

[11] Patent Number: 4,822,335
[45] Date of Patent: Apr. 18, 1989

[54] APPARATUS FOR TREATMENT OF CANCER WITH PHOTODIODE

[75] Inventors: Yoshio Kawai, Musashino; Kazue Endo; Makoto Yoshimura, both of Kawasaki, all of Japan

[73] Assignee: Kureha Kagaku Kogyo Kabushiki Kaisha, Tokyo, Japan

[21] Appl. No.: 94,111

[22] Filed: Sep. 8, 1987

[30] Foreign Application Priority Data

Oct. 29, 1986 [JP] Japan ................. 61-257345

[51] Int. Cl.⁴ .................. A61F 2/38; A61B 17/36
[52] U.S. Cl. ................. 604/20; 128/303.1
[58] Field of Search ............ 604/20; 128/303.1, 395, 128/634, 654

[56] References Cited

U.S. PATENT DOCUMENTS

| | | | |
|---|---|---|---|
| 4,402,318 | 9/1983 | Swartz | 604/20 |
| 4,556,057 | 12/1985 | Hiruma et al. | 604/20 |
| 4,612,007 | 9/1986 | Edelson | 604/20 |
| 4,622,952 | 11/1986 | Gordon | 604/20 |
| 4,622,953 | 11/1986 | Gordon | 604/20 |

FOREIGN PATENT DOCUMENTS 5940869  8/1982  Japan .

*Primary Examiner*—John D. Yasko
*Assistant Examiner*—Kathleen A. Daley
*Attorney, Agent, or Firm*—David G. Conlin; Ronald I. Eisenstein

[57] ABSTRACT

Apparatus for the treatment of a cancerous lesion part by irradiating a light energy from a light source to the cancerous lesion part having absorbed and accumulated in advance therein a photosensitive substance with an affinity for tumors, in which said light source comprises a first photodiode adapted to excite the photosensitive substance from the ground state thereof to a singlet state of higher energy level and a second photodiode adapted to exite an energy level of the photosensitive substance which has transited from the singlet state to a triplet state to a still higher energy level.

23 Claims, 3 Drawing Sheets

APPARATUS FOR TREATMENT OF CANCER WITH PHOTODIODE

This invention relates to an apparatus for the treatment of a cancer by irradiating a light generated from a photodiode such as light-emitting diode or laser diode to a cancerous lesion part in which is absorbed and accumulated in advance a photosensitive substance such as a hematoporphyrin derivative or a compound of phthalocyanine series having an affinity for tumors.

In recent years, studies on the application of the laser to the medical field have been gaining in impetus. Particularly in the field concerning diagnosis and treatment of cancers, growing attention has been focused on the method for the treatment of a cancer, which comprises preparatorily administering a photosensitive substance such as a hematoporphyrin derivative to a cancer-carrying patient thereby causing the photosensitive substance to be selectively absorbed and accumulated in the tumorous area of the patient's body, irradiating the tumorous area with a laser beam thereby exciting the photosensitive substance into liberating a superoxide anion radical ($.O_2^-$), hydrogen peroxide ($H_2O_2$), a hydroxy radical ($.OH$), or a singlet oxygen ($^1O_2$), and utilizing the oxidizing power of the liberated radical or equivalent in destroying cancerous cells. Heretofore, as a laser beam for use in this method of treatment, a continuous wave laser beam such as the argon-excited dye laser has been widely known. Since the energy of a laser beam injected into living tissues is exponentially attenuated relative to the depth of living tissues, however, the low-output continuous beam such as the aforementioned argon-excited dye laser has a small degree of energy penetration to the affected part and, consequently, possesses as a problem the insufficient effect of treatment on a cancerous lesion part of a large size. In this field, therefore, emphasis is placed on the utilization or development of a laser beam source possessing a high output and a high degree of energy concentration. For example, Japanese Patent Application Laying-Open No. 59(1984)-40,869 discloses apparatus for the therapy and diagnosis of a cancer by the use of a pulsating laser beam in the place of a continuous wave laser beam: This method and apparatus for the treatment is expected to attain its full growth in the future in the sense of improving the degree of penetration of the energy of a laser beam to the interior of the lesion part. Incidentally, any apparatus for the treatment of a cancer by the use of a laser beam source entails many problems concerning its practical utility because the device for emission of a laser beam, is voluminous, expensive, troublesome in terms of maintenance and management, and devoid of versatility and because the laser beam source unexceptionally required to possess high energy has the possibility of destroying even normal cells besides the cells in trouble.

The inventors continued a diligent study in search of a breakthrough to the true state of affairs mentioned above. They have consequently found that by using a photodiode as a light source for irradiation of a lesion part having absorbed and accumulated in advance therein a photosensitive substance with affinity for tumors and devising a method for excitation of the aforementioned photosensitive substance, treatment of a cancer can be efficiently carried out even when the continuous wave beam emitted from the photodiode possesses an extremely feeble energy which is one-some tenths to one-some tens-thousandths of the energy of the laser beam. The present invention has been perfected as the result.

Specifically, the present invention which is based on the finding mentioned above provides apparatus for the treatment of a cancerous lesion part with a light energy which is irradiated from a light source to the cancerous lesion part having absorbed and accumulated in advance therein a photosensitive substance with an affinity for tumors, wherein said light source comprises a first photodiode adapted to excite said photosensitive substance from the ground state thereof to a singlet state of a high energy level and a second photodiode adapted to excite an energy level of the photosensitive substance which has transited from said singlet state to a triplet state to a still higher energy level.

Owing to the construction described above, the apparatus of this invention or the treatment of a cancer is inexpensive and, as a whole, is small and light as compared with the therapeutic apparatus using a laser beam source. Whereas the conventional therapeutic apparatus using the laser beam source inevitably requires a patient to approach himself to the apparatus by walking, the apparatus of the present invention can be approximated to the patient (affected part) and enjoys many advantages from the standpoint of clinical therapy.

Moreover, the apparatus of the present invention utilizes a feeble energy radiation source as a light source and, therefore, excels the conventional countertype in terms of the safety from misoperation (erroneous irradiation). Further, as regards the effect of treatment, since the apparatus of this invention effects destruction and exfoliation of tumorous cells from the surface part thereof, it has the advantage that even when a tumor under treatment happens to be large, this apparatus is capable of bringing about complete cure of the tumor in a deep portion without adversely affecting the normal tissue adjacent to the tumor.

Now, the present invention will be described further in detail below with reference to the accompanying drawings.

Figure 1:
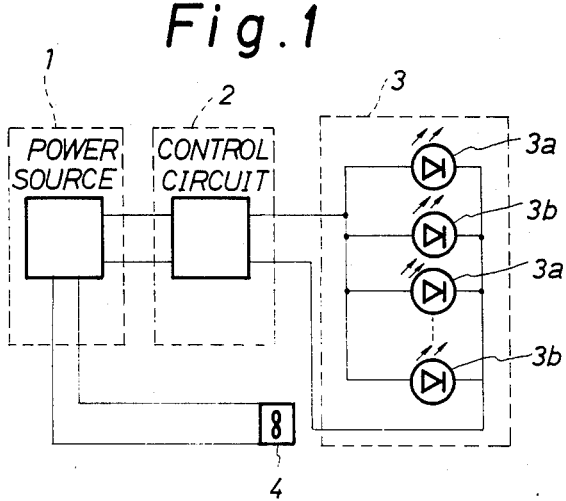
FIG. 1 is a basic circuit diagram of apparatus of this invention for the treatment of a cancer.

In FIG. 1 is shown the basic circuit diagram of the apparatus of this invention for the treatment of a cancer. As a power source 1, for example an AC-DC converter or, where the apparatus is intended as a portable version, a battery is used. A light emission part 3 comprises photodiodes 3a, 3b. One of these two photodiodes is used for exciting a photosensitive substance in the ground state ($S_o$) to a singlet state ($S_n$) and the other photodiode is used for exciting the energy level which has transited from the aforementioned singlet state to a triplet state (T) to a further higher level. The number of these photodiodes 3a, 3b and the manner of their disposition can be freely selected, depending on the position of the area for treatment on a patient's body, the size of a lesion part, the shape of the lesion part, etc. A circuit part 2 is intended to protect or control an overcurrent to the light emission part 3. It is formed of a protective resistance, for example.

The basic circuit shown in FIG. 1, when necessary, may be provided with such an auxiliary device as a fan 4 adapted to deprive the light emission part 3 of the heat generated therein.

Figure 2:
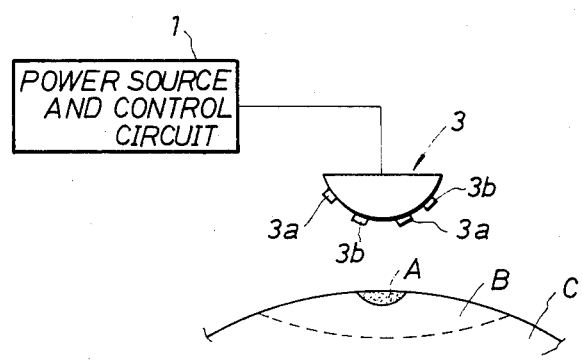
FIG. 2 is a diagram showing a concept of the treatment of a cancerous lesion part by the use of the apparatus of the present invention.

FIG. 2 is a diagram showing a concept of the treatment of a cancerous lesion part by the use of the apparatus of the present invention. In FIG. 2, 1 denotes a power source part and an overcurrent protection part or control circuit part and 3 a light emission part respectively. In the light emission part 3, a plurality of photodiodes 3a, 3b are disposed. Then, A stands for a cancerous lesion part, B for a peripheral part thereof, and C for a normal part respectively.

Preparatory to the actual treatment, a photosensitive substance such as a hematoporphyrin derivative is diluted with a pharmaceutically acceptable diluent and prepared otherwise and administered to a patient by intravenous injection, local injection, or abdominal injection, for example. On elapse of several days after the administration, the photosensitive substance is specifically absorbed and accumulated in the cancerous tissue and ceases to exist substantially in the normal tissue.

At this time, the apparatus of the present invention is operated so as to irradiate the cancerous lesion part with the beam issuing from the photodiodes for necessary treatment. The photodiodes 3a, 3b are suitably selected from light-emitting diodes or laser diodes, depending on the light absorption characteristic of the photosensitive substance being used. Where the photosensitive substance happens to be a hematoporphyrin derivative (HpD: product of Queen Elizabeth Hospital), for example, the combination of light-emitting diodes of GaAsP having a wavelength of 630 nm and light-emitting diodes of GaP having a wavelength of 690 nm proves to be a preferred choice. By irradiating the lesion part simultaneously with the beams from these two kinds of light-emitting diodes, the photochemical reaction of the hematoporphyrin derivative is conspicuously enhanced and the effect of treatment consequently improved. Compounds of phthalocyanine series may be cited as other concrete examples of the photosensitive substance under discussion. This invention, however, does not restrict the photosensitive substance only to those mentioned above.

Figure 3A:
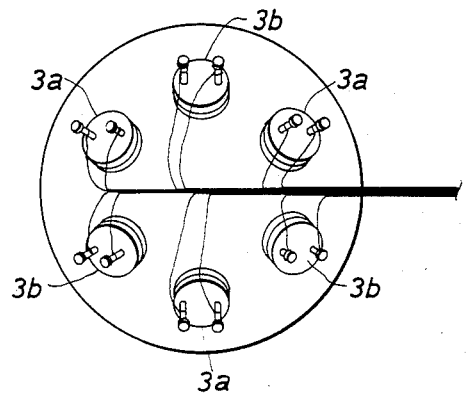
FIG. 3a and FIG. 3b are diagrams illustrating typical embodiment of a light emission part of the apparatus of this invention.
Figure 3B:
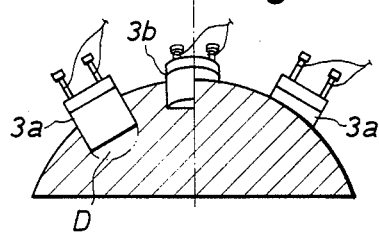

FIG. 3a and FIG. 3b illustrate typical embodiment of the light emission part 3 in the apparatus of this invention for the treatment of a cancer. FIG. 3a is a plan view of the light emission part 3 and FIG. 3b a cross section of the light emission part 3.

In FIG. 3a and FIG. 3b, 3a and 3b stand for photodiodes having different wavelengths. The conventional photodiodes can be utilized in their unmodified form. For the purpose of eliminating the directivity of emission, however, the leading end of each of the photodiodes may be cut out as indicated by the symbol D in FIG. 3b.

The structure of light emission part illustrated in FIG. 3a and FIG. 3b is intended for the treatment of such cancers as various epithelial cancers and mammary cancers. By suitably varying the shape and dimensions of the structure of light emission part, this structure may be adapted to permit treatment of such coeliac cancers as tumors in digestive organs like the gullet, the colon, and the stomach and cancers of the larynx.

Figure 4:
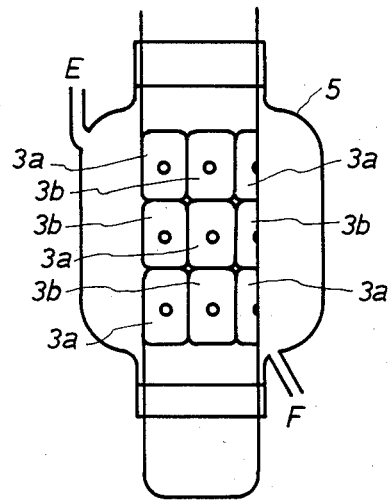
FIG. 4 is a diagram illustrating another typical embodiment of the light emission part in the apparatus of this invention.

FIG. 4 illustrates a typical applicator for the use of the apparatus for endotract or intracavitary treatment. In FIG. 4, 3a and 3b denote photodiodes different in kind from each other and 5 denotes a balloon made of a freely expansible and contractive material such as, for example, silicone rubber and adapted to enclose the photodiodes. This balloon 5 is provided with flow paths E and F for introducing and discharging a coolant such as distilled water, physiological saline water, or olive oil which has a small capacity for light absorption. The balloon 5 advantageously functions in increasing the output of the photodiodes, preventing the normal tissue in the neighborhood of the affected part from damage by burning, and ensuring fixation of the applicator to the affected part. Optionally, the flow path for the coolant may be formed inside the structure of photodiodes.

Now, the effect to be brought about by the use of the apparatus of this invention in the treatment of a cancer will be described below.

The test for the confirmation of this effect was performed as follows.

Preparation of test specimen

In a plastic dish 35 mm in diameter, 0.1 ml of a cancer cell (HeLa-S3) solution having a cell concentration of $2 \times 10^5$ per ml was placed and 2 ml of a culture medium was added and the resultant mixture was left standing at 37° C. for 48 hours under an atmosphere containing 5% of carbon dioxide gas for culture of the cells. The culture medium was prepared by adding blood serum albumin in a concentration of 10% and Kanamycin (product of Meiji Seika Kaisha, Ltd.) in a concentration of 100 $\mu$g/ml to an MEM-Eagle culture solution (product of GIBCO Corp.). After completion of the culture, the supernatant formed in the dish was removed and then 2 ml of a culture solution containing a hematoporpyrin derivative (HpD: product of Queen Elizabeth Hospital) in a concentration of 2 $\mu$g/ml was introduced to continue the culture for two hours under the same conditions as mentioned above. Then, the supernatant formed in the dish at the end of the culture was discarded and the remaining culture broth was washed with 2 ml of an MEM-Eagle culture solution to remove the hematoporphyrin derivative which had not been absorbed and accumulated in the cells. By further adding 2 ml of culture medium to the cleaned remaining culture broth, there was obtained a test specimen.

Irradiation test

In a structure of light emission part illustrated in FIG. 3a and FIG. 3b, five photodiodes (TLS-154; product of Toshiba Limited) having a wavelength of 635 nm were used as 3a and four photodiodes (TLR-145; product of Toshiba Limited) having a wavelength of 690 nm were used as 3b respectively were incorporated to form the apparatus of this invention for the treatment of a cancer. The aforementioned test specimen was set at such a position that the photodiodes are separated by a distance of 8 mm from the upper side of the test specimen. It was irradiated with the beams of light emitted from the photodiodes at an output of 18 mA of a supplied current, to find the relation between the time of irradiation and the ratio of surviving cells. The test specimens subjected to this test were taken as forming one group.

For comparison, an apparatus was formed by incorporating nine photodiodes of a wavelength of 635 nm as 3a and 3b in a similar structure of light emission part. With this apparatus, a comparative test was carried out in the same manner as the test method mentioned above. The test specimens subjected to this comparative test were taken as forming another group.

In the tests described above, a forced air cooling duct was disposed between the plane of light emission and the test specimen for the purpose of preventing the temperature of the test specimen from rising, and the difference of temperature between the outlet and inlet thereof was kept below 0.4° C.

Table 1 shows the relation between the time of irradiation and the ratio of surviving cells in given two groups of test specimens relative to the control group (devoid of irradiation) as determined by the test with the apparatus of this invention and the comparative test.

TABLE 1

|  | Time (hr) | | | | |
| --- | --- | --- | --- | --- | --- |
|  | 3 | 6 | 18 | 24 | 48 |
| Comparative test | 1.0 | 1.0 | 0.88 | 0.91 | 0.81 |
| This invention | 1.0 | 0.98 | 0.84 | 0.75 | 0.41 |

Figure 5:
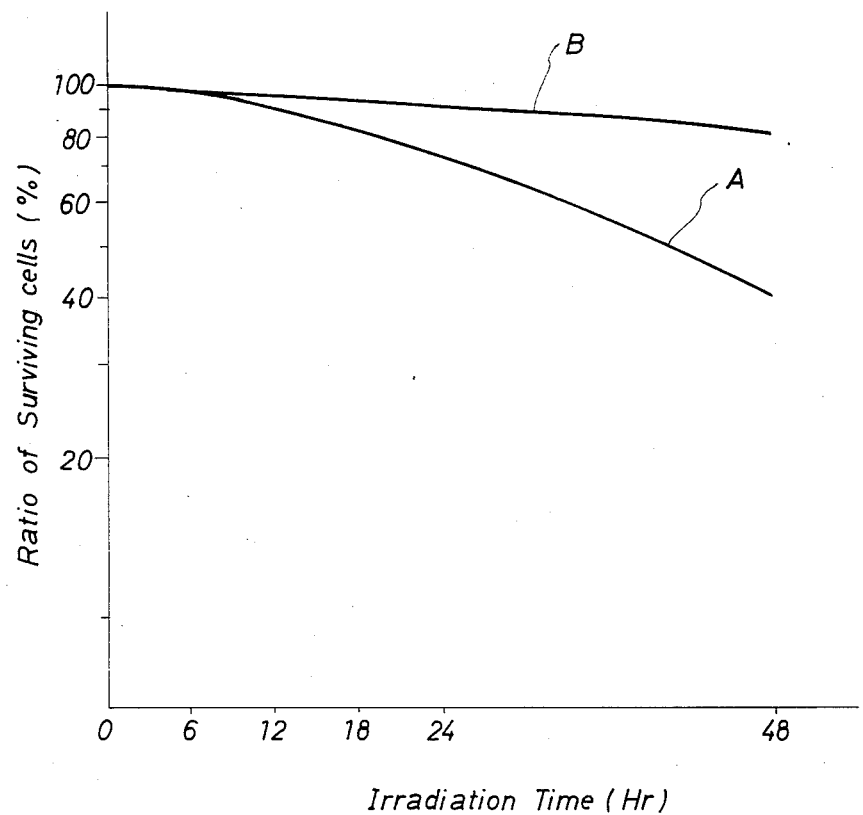
FIG. 5 is a diagram illustrating the relation between the time of irradiation with the beam from a photodiode and the proportion of surviving cells.

By plotting the results of Table 1, there are obtained the two curves shown in FIG. 5.

The curve A represents the results of test obtained by the use of the apparatus of this invention and the curve B those obtained by the use of the apparatus for comparative test.

In FIG. 5, the vertical axis is the scale of the ratio of surviving cells (%) in the respective groups relative to the control group (devoid of irradiation) and the horizontal axis the scale of time (hr) of irradiation.

The data of FIG. 5 evince the effectiveness of the apparatus of this invention.

What is claimed is:

1. Apparatus for treatment of a cancerous lesion part with a light energy which is irradiated from a light source to said cancerous lesion part having absorbed and accumulated in advance therein a photosensitive substance with an affinity for tumors, wherein said light source comprises a first photodiode adapted to excite said photosensitive substance from the ground state thereof to a singlet state of a higher energy level and a second photodiode adapted to excite an energy level of said photosensitive substance which has transited from said singlet state to a triplet state to a still higher energy level, wherein a plurality of pairs of first and second photodiodes are disposed on a curved surface of a spherical-segment shaped support member along the bottom periphery of said support member and projected radially outwardly from said curved surface, any two randomly selected adjacent photodiodes constituting a pair of a first photodiode and a second photodiode.

2. Apparatus for treatment of a cancerous lesion part with a light energy which is irradiated from a light source to said cancerous lesion part having absorbed and accumulated in advance therein a photosensitive substance with an affinity for tumors, wherein said light source comprises a first photodiode adapted to excite said photosensitive substance from the ground state thereof to a singlet state of a higher energy level and a second photodiode adapted to excite an energy level of said photosensitive substance which has transited from said signlet state to a triplet state to a still higher energy level, wherein a plurality of pairs of first and second photodiodes are disposed on a surface on the side of one end of a flexible support member, in a row of photodiodes in a longitudinal direction of the flexible support member and the row of photodiodes in the direction perpendicular to said longitudinal direction, first photodiodes and second photodiodes are invariable positioned adjacently, said first and second photodiodes are surrounded with a freely expansible and contractive balloon fastened at the opposite ends thereof to said support member, said balloon being provided with a flow path for introduction and discharge of a coolant.

3. The apparatus according to claim 2, wherein said flow path for introduction and discharge of a coolant is disposed inside said flexible support member.

4. The apparatus according to any one of claims 1, 2 or 3, wherein said first and second photodiodes are respectively laser diodes.

5. The apparatus according to any one of claims 1, 2 or 3, wherein said first and second photodiodes are respectively light-emitting diodes.

6. The apparatus according to claim 5, wherein said first photodiodes are light-emitting diodes of GaAsP having a wavelength of 630 nm.

7. The apparatus according to claim 5, wherein said second photodiodes are light-emitting diodes of GaP having a wavelength of 690 nm.

8. The apparatus according to claim 1, wherein said light source is connected to a power source through a circuit part adapted to control an overcurrent flowing to said light source.

9. The apparatus according to claim 8, wherein said circuit part comprises a protective resistance.

10. The apparatus according to claim 1, wherein said light source comprises a plurality of first and second photodiodes, which are alternately connected in series.

11. The apparatus according to claim 1, which is provided with cooling means adapted to remove a heat generated in said light source.

12. Apparatus for treatment of a cancerous lesion part with a light energy which is irradiated from a light source to said cancerous lesion part having absorbed and accumulated in advance in said lesion part a photosensitive substance with an affinity to tumors, wherein said light source comprises a first photodiode for emitting a first light which excites said photosensitive substance from the ground state of said photosensitive substance to a singlet state of a higher energy level than said ground state, and a second photodiode for emitting a second light simultaneously with said first light source, which excites an energy level of said photosensitive substance, which has transited from said singlet state to a triplet state, to a higher energy level than said triplet state, said light source being so adapted as to irradiate to said lesion part both first and second lights for the treatment of said lesion part.

13. The apparatus according to claim 12, wherein a plurality of pairs of first and second photodiodes are disposed on a curved surface of a spherical-segment shaped support member along the bottom periphery of said support member and projected radially outwardly from said curved surface, any two randomly selected adjacent photodiodes constituting a pair of a first photodiode and a second photodiode.

14. The apparatus according to claim 12, wherein a plurality of pairs of first and second photodiodes are disposed on a surface on the side of one end of a flexible support member, in a row of photodiodes in a longitudinal direction of the flexible support member and a row of photodiodes in the direction perpendicular to said longitudinal direction, first photodiodes and second photodiodes are invariably positioned adjacently, said first and second photodiodes are surrounded with a freely expansible and contractive balloon fastened at the opposite ends thereof to said support members, said balloon being provided with flow path for introduction and discharge of a coolant.

15. The apparatus according to claim 14, wherein said flow path for introduction and discharge of a coolant is disposed inside said flexible support member.

16. The apparatus according to any one of claims 12 to 16, wherein said first and second photodiodes are respectively laser diodes.

17. The apparatus according to any one of claims 12 to 15, wherein said first and second photodiodes are respectively light-emitting diodes.

18. The apparatus according to claim 17, wherein said first photodiodes are light-emitting diodes of GaAsP having a wave-length of 630 nm.

19. The apparatus according to claim 17, wherein said second photodiodes are light-emitting diodes of GaP having a wavelength of 690 nm.

20. The apparatus according to claim 12, wherein said light source is connected to a power source through a circuit part adapted to control an overcurrent flowing to said light source.

21. The apparatus according to claim 20, wherein said circuit part comprises a protective resistance.

22. The apparatus according to claim 12, wherein said light source comprises a plurality of first and second photodiodes, which are alternately connected in series.

23. The apparatus according to claim 12, which is provided with cooling means adapted to remove a heat generated in said light source.

* * * * *

UNITED STATES PATENT AND TRADEMARK OFFICE
CERTIFICATE OF CORRECTION

PATENT NO. : 4,822,335
DATED : April 18, 1989
INVENTOR(S) : Yoshio Kawai, Kazue Endo, Makoto Yoshimura It is certified that error appears in the above—identified patent and that said Letters Patent is hereby corrected as shown below:

Column 1, line 24, change "$(.O_2^-)$" to read --$(\cdot O_2^-)$--.

Column 1, line 25, change "(.OH)" to read --($\cdot$OH)--.

Column 1, line 52, change "beam, is" to read --beam is--.

Column 2, line 18, change "invention or the" to read --invention for the--.

In Claim 16, line 2, change "to 16" to read --to 15--.

Signed and Sealed this

Thirtieth Day of January, 1990

*Attest:*

JEFFREY M. SAMUELS

*Attesting Officer*   Acting Commissioner of Patents and Trademarks